(12) United States Patent
Small et al.

(10) Patent No.: US 7,223,893 B2
(45) Date of Patent: *May 29, 2007

(54) LINEAR ALPHA-OLEFIN DIMERS POSSESSING SUBSTANTIAL LINEARITY

(75) Inventors: Brooke L. Small, Kingwood, TX (US); Eduardo J Baralt, Kingwood, TX (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 85 days.

This patent is subject to a terminal disclaimer.

(21) Appl. No.: 10/056,137

(22) Filed: Jan. 24, 2002

(65) Prior Publication Data
US 2002/0177744 A1 Nov. 28, 2002

Related U.S. Application Data

(63) Continuation of application No. 09/660,450, filed on Sep. 12, 2000, now abandoned.

(51) Int. Cl.
*C07C 13/00* (2006.01)
(52) U.S. Cl. .................. 585/17; 585/511; 585/510
(58) Field of Classification Search .............. 585/17, 585/511, 510
See application file for complete search history.

(56) References Cited

U.S. PATENT DOCUMENTS

| | | | | |
|---|---|---|---|---|
| 3,346,662 | A * | 10/1967 | Antonsen | 585/512 |
| 4,069,273 | A * | 1/1978 | Komoto | 585/511 |
| 5,955,555 | A | 9/1999 | Bennett | 526/133 |
| 6,103,946 | A | 8/2000 | Brookhart, III et al. | 585/523 |
| 6,291,733 | B1 * | 9/2001 | Small et al. | 585/512 |
| 6,489,497 | B1 | 12/2002 | Brookhart, III et al. | 556/138 |

FOREIGN PATENT DOCUMENTS

WO WO 99/55646 * 11/1999

OTHER PUBLICATIONS

*Highly Active Iron and Cobalt Catalysts for the Polymerization of Ethylene*, Brooke L. Small, Maurice Brookhart, and Alison M.A. Bennett, *Journal of the American Chemical Society*, vol. 120, No. 16, pp. 4049-4050, 1998.

Beach et al.; Linear Dimerization of Propylene and 1-Butene Catalyzed by (n3-4-Cyclooctene-1-yl)-(1,1,1,5,5,5-Hexafluoro-2,4-Pentanedionato)Nickel: Journal of Molecular Cataysis: 1986; vol. 34, pp. 345-354.

* cited by examiner

*Primary Examiner*—Thuan Dinh Dang
(74) *Attorney, Agent, or Firm*—Conley Rose, P.C.; Rodney B. Carroll; K. KaRan Reed

(57) ABSTRACT

Linear 1-butene dimers and other linear alpha-olefin dimers are manufactured in high yield and with high selectivity by coupling of alpha-olefins. The coupling is accomplished by contacting alpha olefins with an iron-based catalyst activated with an aluminum-based co-catalyst. The catalyst is structured to preclude formation of multiple dimer products, and the byproducts of the olefin coupling consist almost exclusively of methyl branched olefin dimers. The dimers have potentially diverse use in areas stretching form pharmaceuticals to plastics. Linear 1-butene dimers may be particularly useful in the production of plasticizer alcohols which may in turn be used to manufacture high quality plastics with reduced leaching.

9 Claims, 5 Drawing Sheets

Fe-based precatalysts for α-olefin dimerization.

LINEAR ALPHA-OLEFIN DIMERS POSSESSING SUBSTANTIAL LINEARITY

This application is a continuation of application Ser. No. 09/660,450 filed on Sep. 12, 2000, now abandoned.

FIELD OF THE INVENTION

This invention relates to linear and mono-branched olefin dimers and to methods of making same.

BACKGROUND OF THE INVENTION

Dimerization reactions are widely used industrially and the dimerization of olefins by transition metals has been widely studied. Some reviews or reports of such studies include, for example, a chapter by Yves Chauvin and Hélène Olivier on "Dimerization and Codimerization" in Applied Homogeneous Catalysis with Organometallic Compounds, VCH, New York (Comils & Herrmann ed. Vol. 1) 258-268 (1996) and a number of articles cited therein.

Many catalysts are known to dimerize olefins, particularly into branched olefins. However, few such catalysts or catalyst systems have shown promising commercial viability due to a variety of limiting factors, including competing side reactions, catalyst cost and activity, lack of selectivity for dimer formation, and severity of the reaction conditions.

The catalysts that are selective for dimer preparation produce mostly vinylidene dimers or di-branched dimers, or they are unselective in product distribution, producing branched, linear, and vinylidene dimers. For example, U.S. Pat. No. 4,658,078, issued Apr. 14, 1987 to Slaugh et al. teaches a process for dimerizing alpha olefins to vinylidene olefins. U.S. Pat. No. 4,973,788, issued Nov. 27, 1990 to Lin et al. teaches a process for dimerizing vinyl-olefin monomers said to have selectivity of at least 85 percent to form vinylidene olefins but at a slow reaction rate requiring a long reaction time.

W. P. Kretschmer, S. I. Troyanov, A. Meetsma, B. Hessen & J. H. Teuben, "Regioselective Homo- and Codimerization of α-Olefins Catalyzed by Bis(2,4,7-trimethylindenyl)yttrium Hydride," 17 Organometallics 284-286 (1998) discusses compounds which are catalysts for various branched dimers including trimers and also for vinylidenes.

H. Heijden, B. Hessen & A. G. Orpen, "A Zwitterionic Zirconocene Alkyl Complex as a Single-Component α-Olefin Dimerization Catalyst," 120 J. Am. Chem. Soc. 1112-1113 (1998) discusses a zwitterionic zirconocene said to be a single-component catalyst that is highly selective although only moderately active for head-to-tail dimerization of α-olefins.

X. Yang, C. Stem, & T. Marks, "Cationic Zirconocene Olefin Polymerization Catalysts Based on the Organo-Lewis Acid Tris(pentafluorophenyl)borane. A Synthetic, Structural, Solution Dynamic, and Polymerization Catalytic Study," 116 J. Am. Chem. Soc. 10015-10031 (1994) teaches among other things a cationic hydrido complex said to be highly active for the catalytic dimerization of propylene to form a mixture of 2-methyl-1-pentene and 2-methyl-2-pentene.

M. Mitkova, A. Tomov, & K. Kurtev, "A Kinetic Study of Propylene Dimerization by Binuclear Nickel-Ylide Complexes in Presence of Diethylaluminum Chloride as cocatalyst," 110 J. Mol. Cat. A.: Chem. 25-32 (1996) discusses propylene dimerization with binuclear nickel-ylide complexes in the presence of diethylaluminum chloride. Various branched-dimer products were obtained.

S. Svejda & M. Brookhart, "Ethylene Oligomerization and Propylene Dimerization Using Cationic (α-Diimine) Nickel(II) Catalysts," 18 Organometallics 65-74 (1999) discusses catalysts prepared from aryl-substituted α-diimine ligands complexed with nickel(II) bromide and activated with aluminum alkyl activators. This article indicates that the active catalysts dimerize propylene generating product mixtures that have roughly equal compositions of n-hexenes and 2-methylpentenes with 2,3-dimethylbutenes as minor products. The catalysts are said to dimerize higher olefins such as 1-butene and 4-methyl-1-pentene very slowly.

Only a few catalysts are known to produce linear alpha-olefin dimers, and these catalysts or catalyst systems generally exhibit low activity and low selectivity. A recent article by B. Ellis, W. Keim and P. Wasserscheid, on "Linear Dimerisation of But-1-ene in Biphasic Mode Using Buffered Chloroaluminate Ionic Liquid Solvents" in Chem. Commun. 337-338 (1999), notes these problems with catalysts for olefin dimerization, but also notes the desirability of obtaining linear olefin dimers, particularly those derived from 1-butene. The article reports some efforts toward improving the activity of known catalysts while retaining dimer selectivity and product linearity.

U.S. Pat. No. 5,196,624, issued Mar. 23, 1993 to Threlkel et al. and U.S. Pat. No. 5,196,625, also issued Mar. 23, 1993 to Threlkel et al. disclose dimerization processes for producing linear and mono-branched $C_{10}$ to $C_{28}$ olefins employing a catalyst mixture comprising a nickel(II) compound, a phosphite compound and an alkyl aluminum halide. These processes are said to have high yields.

Additional and better catalyst systems or improved dimerization methods for making linear alpha-olefin dimers are still needed, particularly if dimers such as linear 1-butene dimers are to ever be commercially viable.

SUMMARY OF THE INVENTION

The present invention provides linear alpha (α-) olefin dimers that may be produced quickly and efficiently without forming significant non-linear byproducts. The mechanism or process for producing these linear alpha olefin dimers requires a coupling of two olefins per dimer. An initial olefin, such as butene for example, undergoes 1,2 insertion, and a second olefin, such as butene for example, undergoes 2,1 insertion. A complex results that beta (β-) eliminates to produce the linear dimer, such as 1-butene dimer for example.

The coupling is facilitated by a transition metal-based catalyst (or pre-catalyst) that has been activated by an aluminum co-catalyst. The intermediary complex formed is an organo-metallic complex.

The aluminum-based co-catalyst is preferably an alumoxane or a Lewis acid/trialkylaluminum combination such as trialkylaluminum/borane. The transition metal-based catalyst is preferably an iron-based catalyst and most preferably selected from the group having one of the six formulas shown in FIG. 2.

The process is preferably carried out under inert atmosphere at a temperature ranging from about zero degrees Centigrade to about eighty degrees Centigrade for these catalysts, although higher temperatures may also be used, depending on the particular catalyst selected. In a batch application, the reaction initially generates heat which may be as high as about eighty degrees Centigrade or higher. This heat of reaction may be controlled by an external water bath or by internal cooling coils. Without cooling, such heat of reaction will generally be sustained until the reaction substrate is depleted. Preferably the temperature is controlled and maintained at a temperature or temperature range selected for the reaction. In a continuous application, as typical for industrial or commercial applications, a continuous feed of catalyst, co-catalyst and reactant feedstock (i.e., olefins) is supplied and the reaction temperature is maintained within a uniform range.

Depending on the metal-catalyst selected and the reaction conditions, the production of linear alpha olefin dimers resulting from the reaction process will range from about thirty percent to about eighty-five percent.

Linear alpha olefin dimers are believed to have many possible diverse uses that have not previously been able to be developed because of prior inefficiencies and difficulties involved in producing such dimers. For example, linear 1-butene dimers will have use in the production of plasticizer alcohols among other things which in turn may be used to make higher quality plasticizing agents for products with less leaching, as particularly needed and useful for example for medical and food packaging applications.

DETAILED DESCRIPTION OF PREFERRED EMBODIMENTS

The present invention provides linear alpha olefin dimers with methyl-branched olefin dimers as the primary or essentially only by-product. That is, other by-products, such as vinylidenes, tri-substituted olefins and alpha olefins will generally comprise less than about five percent of the reaction product and can occur in so little quantity as to be present in only trace amounts. In an alternative embodiment of the invention, the primary byproduct may be another mono-branched olefin dimer or vinylidene instead or a methyl-branched olefin.

Figure 1:
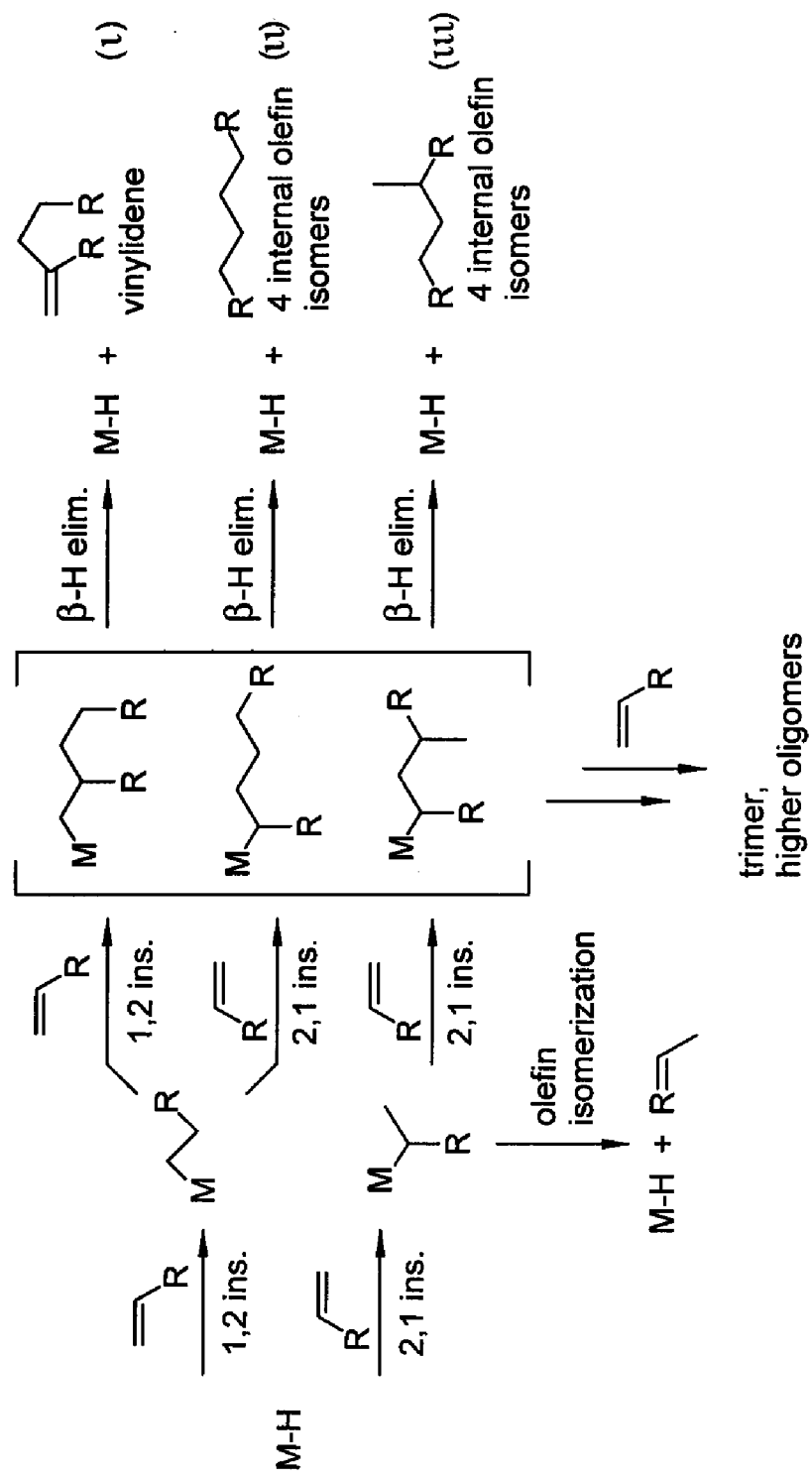
FIG. 1 is a diagram showing three pathways—(i), (ii) and (iii)—for olefin dimerization, the second (ii) of which occurs in the process for making the dimers of this invention and the third (iii) of which results in the formation of byproducts when the dimers of this invention are made. The first pathway (i) results in products commonly seen in prior art olefin dimerization processes but does not occur with the present invention.

Generally, the mechanism or process for making the linear alpha olefin dimers of this invention requires coupling of two olefins per dimer as shown in the second pathway of FIG. 1. The coupling is facilitated by a transition metal catalyst, preferably an iron catalyst, but other metals, such as for example nickel or cobalt may also be used.

A metal hydride resulting from activation of the catalyst or beta-hydrogen elimination is believed to be the active species. This metal hydride gives rise to a primary (1,2) insertion in an alpha olefin to generate a metal-primary alkyl species. To make a linear product, the second olefin exhibits opposite (2,1) regiochemistry of insertion, forming a secondary metal-alkyl bond. Chain transfer leads to a mixture of four linear internal olefin products.

The catalyst should cause the initial 1,2 insertion in the first olefin, as opposed to initial 2,1 insertion, to avoid olefin isomerization and formation of non-linear dimers. Further, the catalyst should preferably prevent or inhibit the formation of vinylidene and branched species. The catalyst should also facilitate rapid beta-hydrogen eliminatior/abstraction and resultant product release on the dimerization timescale to prevent oligomer or polymer production. Preferably, the catalyst is highly active, converting at least about 10,000 and preferably as much as about 20,000 or more moles of olefin per mole of catalyst per hour. Also, the catalyst should not be reactive toward the dimer product, to avoid product isomerizaton or reincorporation.

Figure 2:
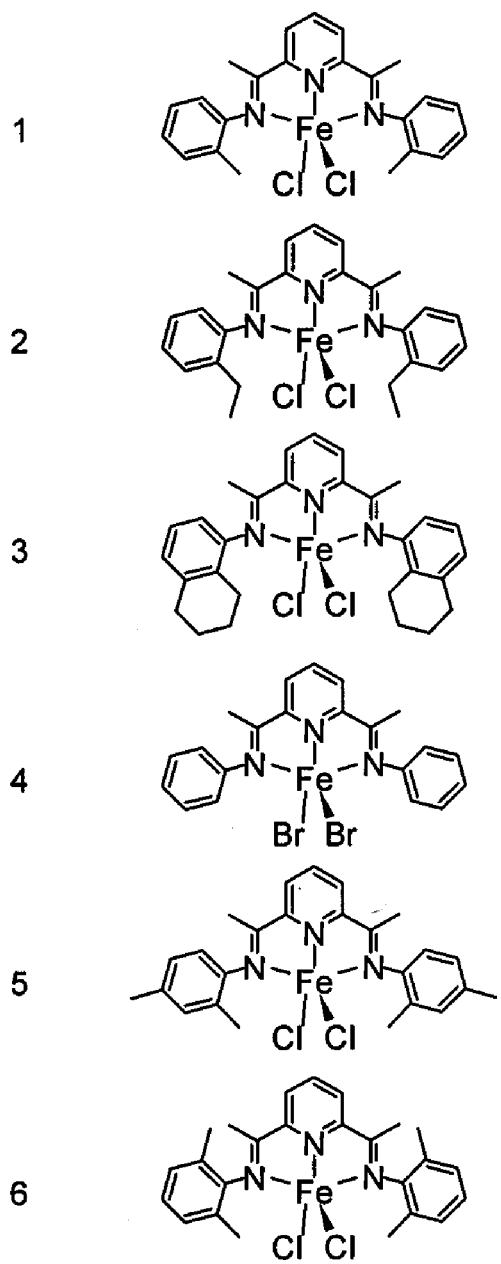
FIG. 2 is a drawing of the chemical formulas of six iron-based catalysts orpre-catalysts for making dimers of this invention.

A group of catalysts exemplified by the six structures in FIG. 2 meet these requirements for a catalyst to make the linear dimers of the invention. Generally, these catalysts are transition metal complexes, preferably tridentate bisimine ligands coordinated to an iron center or a combination of an iron center and aryl rings, either substituted or unsubstituted. Catalysts with less bulky ligands will yield lower molecular weight products as the molecular weight of the products is dependent to a large degree on the size of the ortho substituents on the 2 and 6 positions of the aryl rings of the ligand.

Referring to FIG. 2, complexes 1, 2 and 4 have previously been disclosed as useful catalysts, upon activation, to oligomerize ethylene to linear alpha olefins. Such disclosure, provided in an article by Brooke L. Small and Maurice Brookhart entitled, "Iron-Based Catalysts With Exceptionally High Activities and Selectivities for Oligomerization of Ethylene to Linear α-Olefins," in 120 J. Am. Chem. Soc. 7143-44 (1998), and in PCT patent application no. PCT/US 98/14306 filed Jul. 10, 1998 and published Jan. 21, 1999 as publication no WO99/02472, and especially the description of the synthesis of these catalysts as provided in that PCT patent application, is incorporated herein by reference.

Also referring to FIG. 2, complex 6 has been disclosed as an ethylene and propylene polymerization pre-catalyst. These disclosures by Brooke L. Small, Maurice Brookhart, and Alison M. A. Bennett in "Highly Active Iron and Cobalt Catalysts for the Polymerization of Ethylene," 120 J. Am. Chem. Soc. 4049-50 (1998); Brooke L. Small and Maurice Brookhart in "Polymerization of Propylene by a New Generation of Iron Catalysts: Mechanisms of Chain Initiation, Propagation and Termination," 32 Macromolecules 2120-32 (1999); and in PCT patent application Ser. No. PCT/US/98/ 00316, filed Jan. 12, 1998, and published Jul. 16, 1998 as publication no. WO9830612, and by Brooke L. Small in his University of North Carolina Doctoral Dissertation, *Diss. Abstr. Int.*, B, 1999, 59(12), and especially the description of the synthesis of this catalyst as provided in said Macromolecules article, are incorporated herein by reference.

For use as catalysts in experiments discussed below, these complexes 1, 2, 3, 4, 5, and 6 of FIG. 2 were prepared as disclosed in the references cited above or as discussed in the experimental section below.

The transition metal catalysts, as exemplified by the structures in FIG. 2 for making the dimers of this invention, are activated by an aluminum-based co-catalyst. Alumoxanes or Lewis acid/trialkylaluminum combinations, such as trialkylaluminum/borane, are preferred co-catalysts.

Preferred reaction conditions for making the dimers of this invention are an inert atmosphere and room temperature, although a wide range of temperatures may be used. In a batch operation or for batch preparation, addition of the co-catalyst to the metal catalyst quickly increases the heat of the reaction, which will be sustained until the substrate is depleted unless earlier cooled. Cooling may be accomplished with an exterior cooling bath or interior cooling coils. Later, after the initial exothermic reaction has occurred and the reactants cooled, heating may be desired to maintain a desired reaction temperature for dimerization. In a continuous operation or process, as more typically seen in industry or in commercial applications, the catalyst, co-catalyst and olefin feedstock are fed continuously and the reaction temperature is maintained within a selected range.

The iron catalysts are active over a wide temperature range, from about zero degrees Centigrade to about eighty degrees Centigrade or higher, although their activity decreases with decreasing temperature. As the catalysts' activities decrease at lower temperatures, their selectivity for forming linear alpha olefin dimer product increases. This higher linear selectivity at lower temperature suggests an increased selectivity for primary (1,2) olefin insertion in the first dimerization step.

Figure 3:
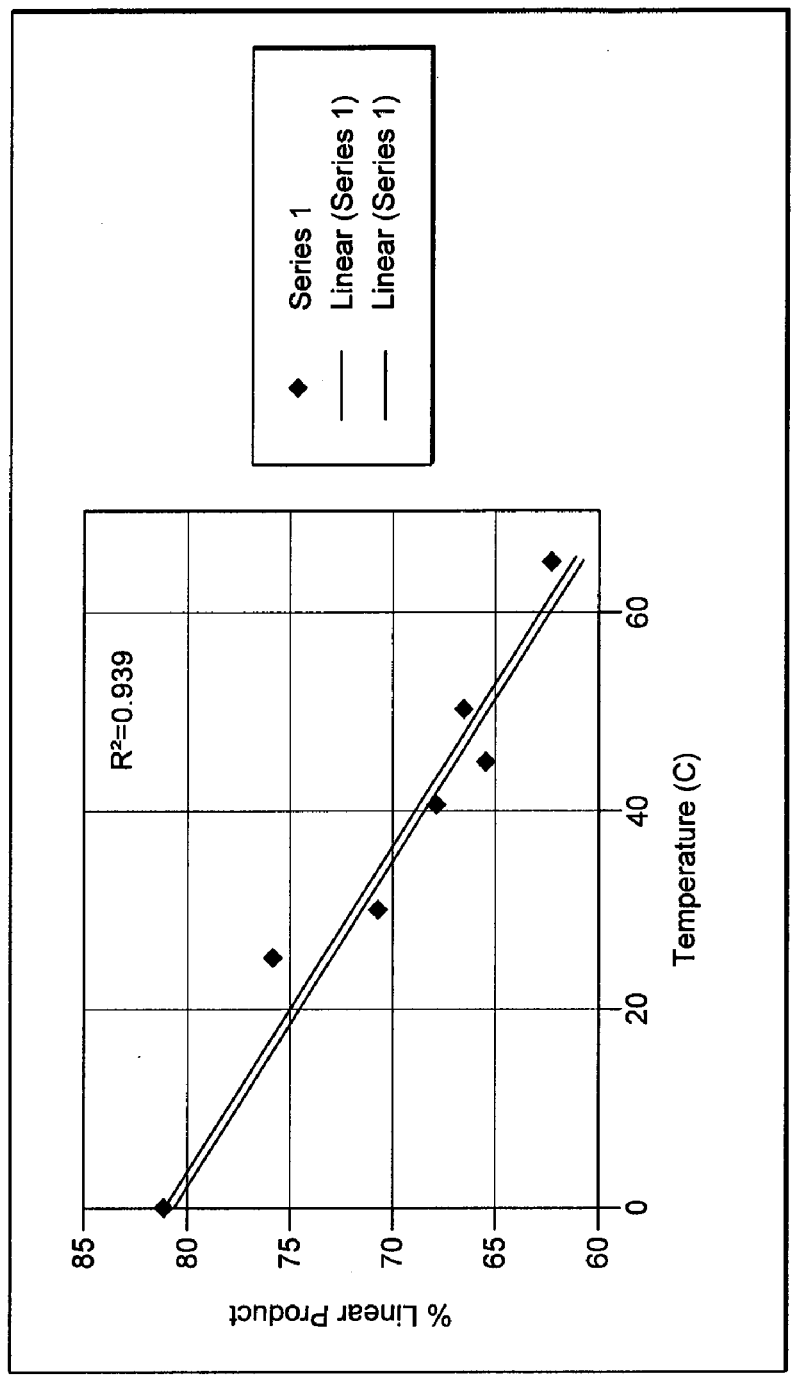
FIG. 3 is a plot showing the yield of linear alpha-olefin dimers as a function of reaction temperature.

Table I shows results of a number of dimerization reactions with the catalysts of FIG. 2. FIG. 3 plots the data for yield of linear alpha olefin dimers of the invention versus temperature of reaction for reactions with the first catalyst, complex 1, in FIG. 2. The temperatures plotted in FIG. 3 and listed in Table I reflect the maximum temperatures that the reactions were allowed to reach. In most cases, these temperatures were maintained for about fifteen minutes to about thirty minutes with cooling, until substrate depletion caused a gradual drop in the temperature. External heating was then used to maintain the desired temperature. The plot of FIG. 3 shows the linear selectivity for linear product at higher temperatures.

As the catalysts' activities increase at higher temperatures, the lifetimes of the catalysts appear to decrease. As Table I shows (entries 10, 15-17), linear alpha olefin dimer product yields of over seventy percent were achieved with reaction temperatures in the range of about 40 to about 50 degrees Centigrade.

All other conditions being equal, different catalysts will yield different percentages of linear alpha olefin dimers. As shown in Table I, catalysts 1, 2, 3 and 5 of FIG. 2 produced mostly linear internal dimers of the invention, while catalyst 4 gave approximately the opposite distribution, with methyl branched internal olefins as the predominant species (as can be seen in entries 6, 8, and 9 in Table I).

Unlike catalysts 1, 2, 3, and 5, catalyst 4 has no alkyl substituents on the aryl rings. Also unlike catalysts 1, 2, 3, and 5, catalyst 4 promoted substantial isomerization in the un-dimerized substrate, thus producing internal olefins. Preferably isomerization does not occur when making the dimers of this invention and generally an advantage of this invention is that remaining or undimerized olefin can be recycled into the process for making the dimers of the invention.

Without wishing to be limited by theory, such isomerization by catalyst 4 may possibly be explained in two ways. First, the non-bulky aryl rings of catalyst 4 may allow the initial insertion to proceed rapidly in comparison to or relative to the second insertion, which causes the rate of beta-hydrogen elimination from the initial insertion to become even more competitive with the second step (olefin addition). Also, since the first step is more likely to proceed with 2, 1 regiochemistry, reversible beta-hydrogen elimination at this stage is believed to result in more isomerized product.

Regardless of the exact reason for increased isomerization by catalyst 4, the increase in methyl-branched dimers from this catalyst shows that the regio regularity of the first olefin insertion step generally decreases with decreasing steric bulk on the ligand. However, the bulkiest of the six catalysts of FIG. 2, catalyst 6, showed only a mild increase in selectivity while its activity dropped precipitously over time. Table 1, entry 27, for this catalyst, shows a linear dimer yield of seventy-four percent at forty degrees Centigrade but the conversion rate dropped to less than ten percent after twenty-four hours.

The exact linear dimers produced with the catalysts will vary with the particular feedstocks. Generally, any olefin or neat monomer with accessible double bond in the alpha position may be used as the initial olefin and any alpha olefin or neat monomer may be used as the second olefin. Propylene tends to polymerize rather than result in dimers according to this invention with the catalysts listed in FIG. 2. However, the principles of the invention are believed applicable to propylene with a suitable catalyst. A surprising aspect of this invention is that some catalysts known to be useful for preparing oligomers, particularly propylene (and ethylene) oligomers, as discussed for example in Brooke L. Small's University of North Carolina Doctoral Dissertation, *Diss. Abstr. Int., B.,* 1999, 59 (12), can effectively be used to prepare dimers.

Suitable feedstocks for producing the dimers of this invention are further exemplified by the experiments discussed below:

Experimental

Materials

Anhydrous tetrahydrofuran (THF) and methanol were purchased from Aldrich and used without further purification. Anhydrous cyclohexane was purchased from Aldrich and stored over molecular sieves. Alpha olefins 1-butene, 1-hexene and 1-decene were obtained as commercial grades of Chevron Chemical Company's Gulftene 4, Gulftene 6 and Gulftene 10, respectively. Alpha olefin 1-pentene was purchased from Aldrich. All alpha olefins were dried over molecular sieves. MMAO-3A and MAO-IP were purchases from Akzo Nobel. MAO was obtained from Albemarle Corporation. Tris-(pentafluorophenylborane), 2,6-diacetylpyridine, iron(II)chloride tetrahydrate, and all substituted anilines were purchased from Aldrich and used without further purification.

Synthesis of Ligands for Catalysts 3 and 5 of FIG. 2

2,6-bis[1-(5,6,7,8-tetrahydronaphthylimino)ethyl]pyridine (for Catalyst 3)

Chemicals 2,6-Diacetylpyridine (1.0 g, 6.1 mmol) and 1-amino-5,6,7,8-tetrahydronaphthalene (3.6 g, 24.5 mmol) were dissolved in a round-bottom flask, to which 50 ml of anhydrous methanol were added. Three drops of glacial acetic acid were added, and the flask was sealed. After stirring the solution for two days, a yellow solid was collected and re-crystallized from methanol to give 760 mg (30%) of the desired ligand for catalyst 3. H NMR ($C_6D_6$) δ 8.48 (d, 2), 7.30 (t, 1), 7.10 (m, 2), 6.85 (d, 2), 6.56 (d, 2).

2,6-bis[1-(2,4-dimethylphenylimino)ethyl]pyridine (for Catalyst 5)

Chemicals 2,6-Diacetylpyridine (2.0 g, 12.3 mmol) and 2,4-dimethylaniline (8.9 g, 73.7 mmol) were dissolved in a round-bottom flask with a stirring bar, to which 50 ml of anhydrous methanol were added. Three drops of glacial acetic acid were added, and the flask was sealed. After stirring the solution for three days, 3.79 g (84%) of a yellow solid were collected and identified as the desired ligand for catalyst 5. H NMR (CDCl$_3$) δ8.39 (d,2), 7.85 (t, 1), 7.05 (s, 2), 7.00 (d, 2), 6.60 (d, 2).

nitrogen and charged with the liquid monomer. Stirring was begun to effectively slurry the sparingly soluble catalyst (or pre-catalyst) in the neat monomer. After several minutes, the aluminum co-catalyst was added via syringe. Many of the reactions were activated at or near room temperature, but the exothermic nature of the reaction often caused the temperature to rise significantly, as reported in Table I.

TABLE 1

Results for the Dimerization of α-Olefins

| Entry | Catalyst | Loading (mg) | Co-catalyst | Al/Fe ratio | α-olefin monomer | Amount (ml) | React. length | React. % temp. (20 C.) | % conv. | Yield (g) | TON | % dimer | % linear internal | % methyl branched |
|---|---|---|---|---|---|---|---|---|---|---|---|---|---|---|
| 1 | 1 | 1.0 | MMAO | 810 | C6 | 20 | 3 h | 25 | 21 | 2.8 | 15,600 | 92 | 76 | 23 |
| 2 | 1 | 1.0 | MMAO | 810 | C6 | 20 | 3 h | 0 | 9 | 1.2 | 6,700 | 85 | 81 | 18 |
| 3 | 1 | 5.1 | MMAO | 560 | C4 | 200 | 1 h | 30 | 22 | 26.0 | 42,600 | 85 | 71 | 28 |
| 4 | 2 | 5.9 | MMAO | 440 | C6 | 50 | 1 h | 30 | 28 | 9.4 | 9,400 | 87 | 71 | 28 |
| 5 | 1 | 11.7 | MMAO | 420 | C6 | 200 | 2 h | 65 | 29 | 39.3 | 18,700 | 85 | 63 | 36 |
| 6[a] | 4 | 10.7 | MMAO | 340 | C6 | 100 | 30 m | 82 | 58 | 39.2 | 23,100 | 96 | 27 | 70 |
| 7 | 1 | 10.0 | MMAO | 240 | C4 | 200 | 1 h | 40 | 58 | 70.6 | 59,000 | 83 | 71 | 28 |
| 8 | 4 | 4.3 | MMAO | 660 | C6 | 100 | 2 h | 20 | 8 | 5.6 | 8,200 | 95 | 34 | 65 |
| 9 | 4 | 6.0 | MMAO | 480 | C6 | 100 | 1 h | 50 | 44 | 29.8 | 31,300 | 96 | 29 | 70 |
| 10 | 1 | 10.5 | MMAO | 480 | C6 | 200 | 5 h | 40 | 70 | 93.9 | 49,800 | 83 | 66 | 33 |
| 11 | 5 | 10.5 | MMAO | 510 | C6 | 200 | 1 h | 40 | 64 | 86.1 | 48,400 | 85 | 65 | 34 |
| 12 | 5 | 6.8 | MMAO | 390 | C6 | 100 | 2 h | 0 | 33 | 22.3 | 19,400 | 83 | 80 | 19 |
| 13 | 5 | 6.3 | MMAO | 430 | C5, C6[b] | 47, 53 | 1 h | 40 | 65 | 42.8 | 43,700 | 85 | 64 | 35 |
| 14 | 3 | 5.5 | MMAO | 490 | C6 | 100 | 1 h | 40 | 36 | 24.1 | 28,600 | 90 | 71 | 28 |
| 15 | 5 | 26.5 | MMAO | 80 | C6 | 200 | 16 h | 50 | 76 | 102.2 | 22,800 | 85 | 63 | 36 |
| 16 | 1 | 15.3 | MMAO | 220 | C10 | 100 | 2 h | 45 | 74 | 54.7 | 11,000 | 85 | 66 | 33 |
| 17 | 1 | 10.0 | MMAO | 100 | C6 | 100 | 16 h | 50 | 70 | 46.9 | 26,100 | 87 | 67 | 32 |
| 18 | 1 | 10.0 | TEA, F$_{15}$B/25 mg | 140 | C6 | 200 | 2 h | 45 | 31 | 43.1 | 24,000 | 95 | 66 | 33 |
| 19 | 1 | 10.0 | TEA, F$_{15}$B/25 mg | 100 | C6 | 200 | 2 h | 45 | 29 | 39.7 | 22,100 | 94 | 69 | 30 |
| 20 | 1 | 10.0 | TEA, F$_{15}$B/25 mg | 100 | C6 | 200 | 2 h | 30 | 44 | 59.2 | 33,000 | 93 | 71 | 28 |
| 21 | 1 | 10.0 | TEA, F$_{15}$B/25 mg | 70 | C6 | 200 | 2 h | 30 | 43 | 59.1 | 32,900 | 93 | 70 | 29 |
| 22 | 1 | 50.0 | MMAO | 250 | C20–24 | 1 kg | 26 h | 50 | 31 | 310 | ~9,500 | 84 | 68 | 31 |
| 23 | 1 | 10.0 | TIBAL, F$_{15}$B/25 mg | 120 | C6 | 200 | 2 h | 40 | 36 | 48.5 | 27,000 | 94 | 67 | 32 |
| 24 | 1 | 30.0 | MMAO | 80 | C4 | 400 | 1.75 h | 40 | 81.5 | 209 | 58,100 | 85 | 68 | 31 |
| 25 | 1 | 30.0 | MAO-IP | 105 | C4 | 400 | 70 m | 40 | 57 | 145 | 40,500 | 85 | 68 | 31 |
| 26 | 1 | 100.0 | MAO | 100 | C4 | 2300 | 3 h | 40 | 42.7 | 629 | 52,500 | 84.6 | 68.7 | 31.3 |
| 27 | 6 | 14.0 | MMAO | 250 | C6 | 100 | 24 h | 40 | 7.8 | 5.3 | 2,200 | >95 | 74 | 25 |
| 28 | 1 | 100.0 | MMAO | 85 | C4 | 2300 | 3 h | 40 | 56.9 | 785 | 65,600 | 83.1 | 68 | 31 |

[a]Catalyst 4 causes substantial isomerization of the non-dimerized olefin.
[b]Co-dimerization using 1-pentene and 1-hexene in equimolar amounts. GC analysis revealed that equimolar amounts (± 5%) of each monomer were incorporated into the resultant dimers and trimers Synthesis of Comlplexes (Catalysts) of FIG. 2

The ligand for complex 3—2,6-bis [1-(5,6,7,8-tetrahydronaphthylimino)ethyl]pyridine—and the ligand for complex 5—2,6-bis [1-(2,4 dimethylphenylimino)ethyl]pyridine—were prepared as discussed in the experimental section above. The ligands for catalysts 1,2,4, and 6 were prepared as discussed in the references cited above. After preparation, each ligand was separately added in slight excess to iron(II)chloride tetrahydrate in tetrahydrofuran (THF). After precipitation with pentane, the complexes were isolated by filtration for use as catalysts.

Dimerization of 1-hexene and Liquid Monomers

A two-necked flask with a stirbar was fitted with a reflux condenser on one neck and a thermocouple with the appropriate adapter on the other neck. The apparatus was heated under vacuum, then filled with nitrogen. The condenser was then removed under positive nitrogen flow and the catalyst (or pre-catalyst) (selected from the structures of FIG. 2) was added quickly. The flask was back-filled three times with nitrogen and charged with the liquid monomer. Stirring was begun to effectively slurry the sparingly soluble catalyst (or pre-catalyst) in the neat monomer. After several minutes, the aluminum co-catalyst was added via syringe. Many of the reactions were activated at or near room temperature, but the exothermic nature of the reaction often caused the temperature to rise significantly, as reported in Table I.

Temperatures were monitored using a thermocouple, and the temperatures listed in Table I represent the maximum temperatures achieved in the reaction. In some cases the exotherm was controlled by a water bath. After reaching the maximum temperature in each reaction, a cooling process was observed, and heating was required to maintain the desired reaction temperature.

Dimerization of 1-butene

A Zipperclave reactor was heated under vacuum at 50 degrees Centigrade for several hours. The reactor was cooled to room temperature under nitrogen. The catalyst (or pre-catalyst) (selected from the structures of FIG. 2) was then quickly added to the reactor, and the reactor was resealed and placed under vacuum. A dual-chambered glass sample charger was then attached to the injection port of the reactor. From the first chamber a small amount of cyclohexane (internal standard, usually about 20 ml) was added. From the second chamber more cyclohexane (usually about 10 ml) and the aluminum co-catalyst were added. The reactor was then quickly sealed and charged with liquid butene. (Cyclohexane serves as an inactive/inert catalyst carrier.) The reactor was further pressurized with at least 100 psi of nitrogen to keep the butene in the liquid phase. The reaction was stirred rapidly, and the temperature was monitored using a thermocouple.

Product Analysis

Figure 4:
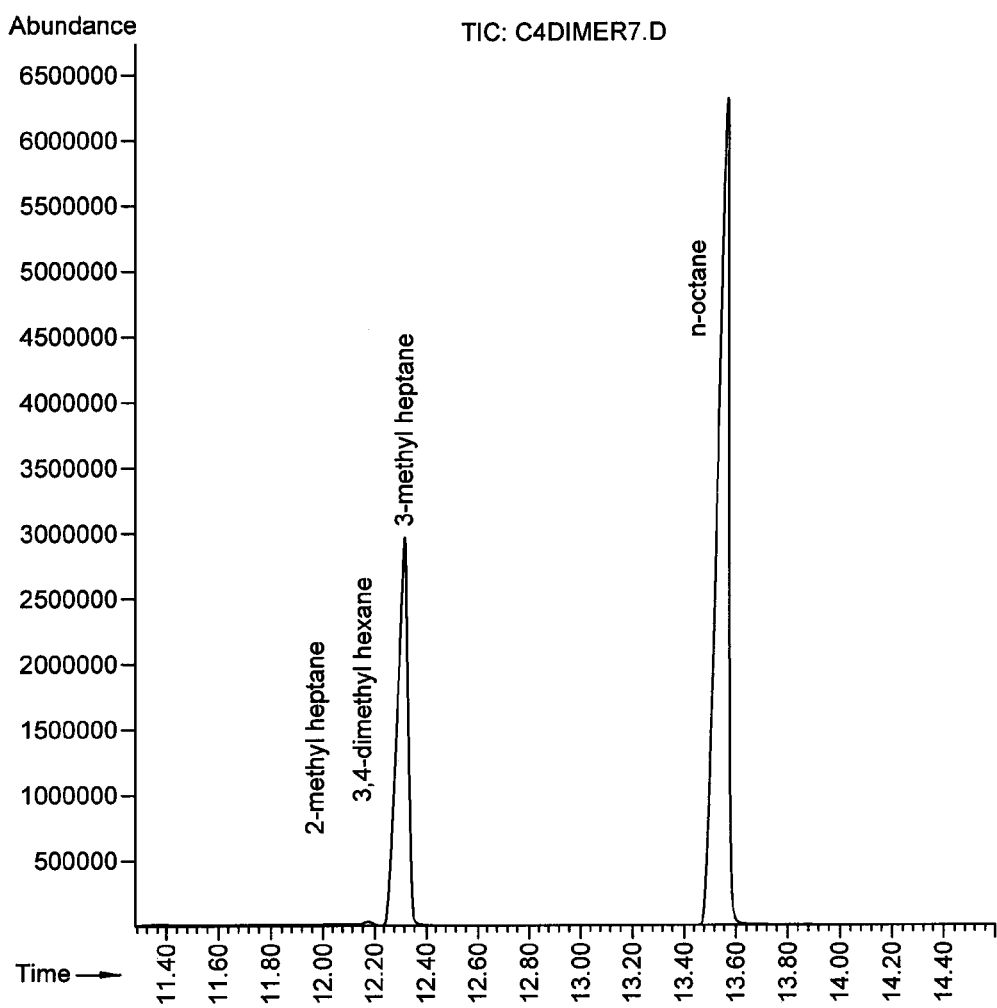
FIG. 4 is a gas chromatograph trace of hydrogenated 1-butene dimers made by the first catalyst of FIG. 2.
Figure 5:
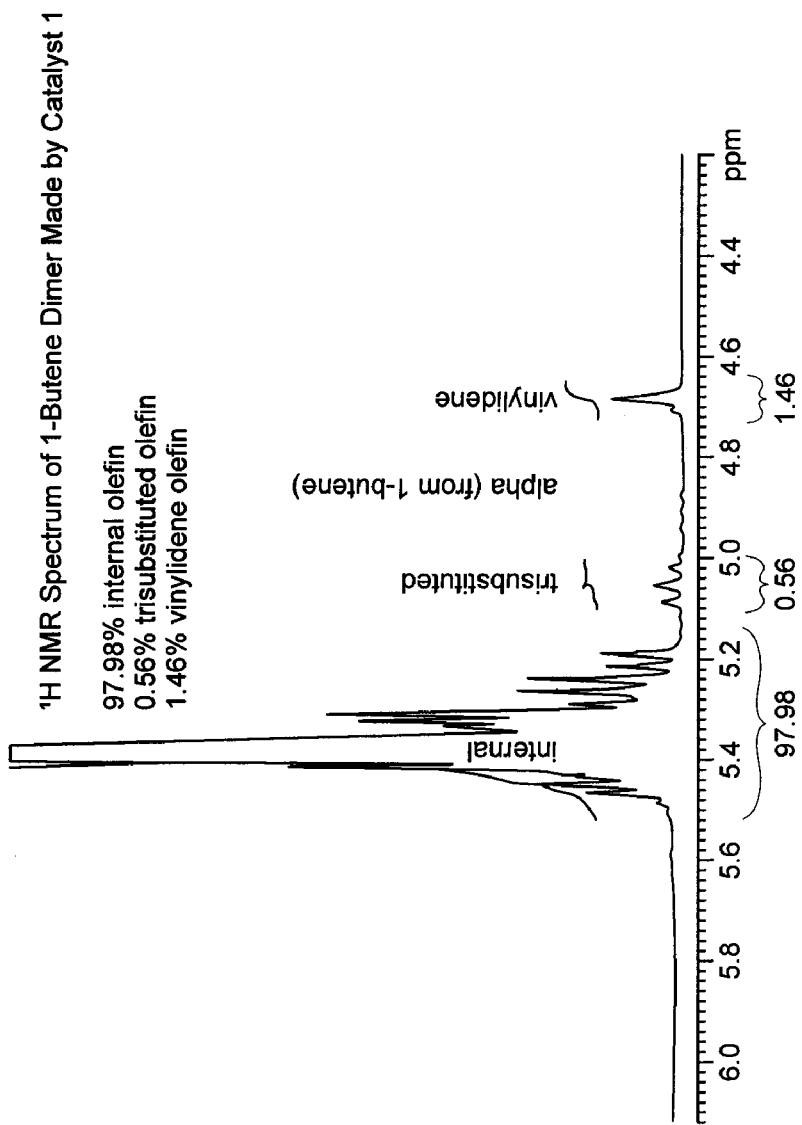
FIG. 5 is an H NMR spectrum of a 1-butene dimer made by the first catalyst of FIG. 2.

The aluminum co-catalysts were removed by pouring the liquid products into a water wash. After removal of the co-catalysts, the products were analyzed by gas chromatography (GC). A Hewlett Packard 6890 Series CG System with an HP-5 50 m column with a 0.2 mm inner diameter was used for dimer as well as alpha-olefin characterization. Chrom Perfect™ Version 4 from Justice Laboratory Software was used to analyze the collected data. GC analysis showed clear separation of the linear from the branched species, and hydrogenation of the products confirmed these results. An example of such analysis is shown in FIG. 4. C NMR and H NMR were used to confirm the internal olefin content in the products, with only about one percent of vinylidene products present. An example of such an H NMR spectrum is shown in FIG. 5.

The conversions and yields were determined by comparing the product to the internal standard integrals, and by assuming equal response factors of the standard and the products. For the hexene dimerization experiments, 1-hexene was the internal standard, and for the butene experiments cyclohexane was used. The approximate density for 1-butene of 0.60 g/ml is included for reference. As shown in Table 1, the dimerization product comprises linear internal dimers, methyl branched dimers, and unreacted monomer. The linear internal dimers may comprise from 27 to 85 weight percent of the dimers present in the dimerization product. The dimerization product may comprise from 18.5 to 80 weight percent unreacted monomer. The dimerization product may further comprise less than about five weight percent vinylidene or tri-substituted olefins.

Hydrogenation of Olefinic Products

The olefinic products in both the dimerization and the alpha-olefin reactions were hydrogenated in a Zipperclave™ reactor at 115 degrees Centigrade and 400 psig hydrogen using HTC Ni 500 catalyst from Crosfield.

The foregoing description of the invention is intended to be a description of a preferred embodiment. Various changes in the details of the described product and process can be made without departing from the intended scope of this invention as defined by the appended claims.

We claim:

1. A product made by a process comprising coupling of an initial olefin and a second olefin to produce dimers, wherein the product of the process comprises (a) dimers, from 27 to 81 weight percent of which are linear internal dimers, (b) from 18.5 to 80 weight percent initial and second olefins, and (c) less than about five weight percent vinylidene or tri-substituted olefins where the at least 83% weight percentage of produced product are dimers.

2. The product of claim 1 wherein the coupling is a head to head coupling accomplished by a 1,2 insertion in the initial olefin followed by a 2,1 insertion in the second olefin resulting in a complex which beta-eliminates to produce the linear internal dimers.

3. The product of claim 2 wherein the coupling further results in byproducts comprising methyl-branched olefin dimers.

4. The product of claim 3 wherein the byproducts of the process further comprise olefin trimers.

5. The product of claim 1 wherein the initial olefin is butene and the second olefin is butene and the dimer is a 1-butene dimer.

6. The product of claim 1 wherein the initial olefin and the second olefin are selected from the group consisting of alpha olefins consisting of about five to about eight carbon atoms.

7. The product of claim 1 wherein the initial olefin and the second olefin are selected from the group consisting of alpha olefins consisting of about nine or more carbon atoms.

8. A feedstock for the production of oxoalcohols comprising the dimer product of claim 1.

9. The product of claim 1 wherein the dimers comprise equal to or greater than about 60 weight percent linear internal dimers.

* * * * *